(12) United States Patent
Geiger et al.

(10) Patent No.: US 7,648,481 B2
(45) Date of Patent: Jan. 19, 2010

(54) SYRINGE TIP CAP AND METHOD FOR PRODUCING A SYRINGE TIP CAP

(75) Inventors: Andreas Geiger, Hiddenhausen (DE); Frank Wittland, Enger (DE)

(73) Assignee: Buende Glas GmbH, Buende (DE)

( * ) Notice: Subject to any disclaimer, the term of this patent is extended or adjusted under 35 U.S.C. 154(b) by 787 days.

(21) Appl. No.: 11/141,292

(22) Filed: May 31, 2005

(65) Prior Publication Data

US 2006/0178627 A1 Aug. 10, 2006

(30) Foreign Application Priority Data

May 29, 2004 (EP) .................. 04012833
May 12, 2005 (EP) .................. 05010397

(51) Int. Cl.
*A61M 5/00* (2006.01)
(52) U.S. Cl. ...................... 604/110; 604/263
(58) Field of Classification Search .......... 604/110, 604/111
See application file for complete search history.

(56) References Cited

U.S. PATENT DOCUMENTS

| | | | |
|---|---|---|---|
| 4,720,285 A * | 1/1988 | Pickhard ............ 604/192 |
| 5,611,785 A * | 3/1997 | Mito et al. ............ 604/239 |
| 6,190,364 B1 | 2/2001 | Imbert | |
| 7,255,689 B2 * | 8/2007 | Westbye ............... 604/500 |
| 2003/0120209 A1 * | 6/2003 | Jensen et al. ........... 604/110 |
| 2003/0199822 A1 * | 10/2003 | Alchas et al. .......... 604/117 |
| 2003/0212369 A1 * | 11/2003 | Kobayashi ............. 604/197 |
| 2003/0212372 A1 * | 11/2003 | Bills et al. ............ 604/236 |
| 2004/0116858 A1 * | 6/2004 | Heinz et al. ........... 604/111 |
| 2004/0225258 A1 * | 11/2004 | Balestracci ............ 604/111 |

* cited by examiner

*Primary Examiner*—Nicholas D Lucchesi
*Assistant Examiner*—Gerald Landry, II
(74) *Attorney, Agent, or Firm*—Laurence A. Greenberg; Werner H. Stemer; Ralph E. Locher

(57) ABSTRACT

A syringe tip cap sealingly closes a distal opening of a syringe body. The syringe tip cap has a fastening ring which can be placed and fastened on the syringe body about the distal opening, and a closure cap which closes the distal opening in a sealed manner and is connected releasably to the fastening ring. The fastening ring has a locking means device that locks together with a locking device of the closure cap. The locking device of the fastening ring and the locking device of the closure cap are configured in such a way that they cannot be unlocked without sustaining damage. The syringe tip cap may be produced in a two-component injection molding process.

17 Claims, 12 Drawing Sheets

SYRINGE TIP CAP AND METHOD FOR PRODUCING A SYRINGE TIP CAP

BACKGROUND OF THE INVENTION

Field of the Invention

The invention relates to a syringe tip cap for closing a distal opening of a syringe body in a sealed manner, and to a method for producing such a syringe tip cap.

U.S. Pat. No. 6,190,364 describes such a syringe tip cap for a syringe body. The syringe body has a distal tip and a distal opening extending through the latter, such that an injection liquid located in the syringe body can exit the syringe body via the distal opening. The syringe comprises a fastening ring, or luer collar, which is formed in one piece with the syringe or is placed on the distal tip of the syringe body and connected fixedly thereto. The fastening ring has thread elements which interact with thread elements of a two-part closure cap in order to hold the closure cap on the fastening ring. In use, the closure cap encloses the distal tip and closes and seals off the distal opening of the syringe body.

To inject the injection liquid, the closure cap is unscrewed from the fastening ring and a syringe needle is secured on the fastening ring and thus on the syringe body in such a way that a needle opening extending through the syringe needle is in fluidic communication with the distal opening of the syringe body. To secure the syringe needle on the fastening ring, the syringe needle is connected to a thread element which interacts with the thread element of the fastening ring.

To ensure that possible use of or tampering with the syringe content is made evident, the syringe tip cap according to U.S. Pat. No. 6,190,364 comprises a sealing strip which is connected permanently both to the fastening ring and also to the closure cap, such that the sealing strip tears when the closure cap is detached from the fastening ring.

A disadvantage of this syringe tip cap is that producing three separate parts (two-part closure cap, sealing element) and joining these parts together to form a syringe tip cap is an elaborate procedure.

SUMMARY OF THE INVENTION

It is accordingly an object of the invention to provide a syringe tip cap and a production method which overcome the above-mentioned disadvantages of the heretofore-known devices and methods of this general type and which provides for a syringe tip cap for closing a distal opening of a syringe body in a sealed manner, which syringe tip cap ensures that any use of or tampering with the syringe content is made evident, and which syringe tip cap is also of a simplified structure and is thus easier to produce.

With the foregoing and other objects in view there is provided, in accordance with the invention, a syringe tip cap for sealingly closing a distal opening of a syringe body, the syringe tip cap comprising:

a fastening ring to be arranged and fastened on the syringe body about the distal opening; and a closure cap releasably connected to the fastening ring and sealingly closing the distal opening;

the fastening ring having a first locking device interlocked with a second locking device of the closure cap, and wherein the first locking device and the second locking device are configured not to be unlocked without sustaining damage and, after unlocking, cannot be returned to an initial locked state.

In other words, the objects of the invention are achieved by a syringe tip cap for closing a distal opening of a syringe body in a sealed manner, the syringe tip cap having a fastening ring which can be arranged and fastened on the syringe body about the distal opening, and a closure cap which closes the distal opening in a sealed manner and is connected releasably to the fastening ring, said fastening ring comprising a locking means which locks together with a locking means of the closure cap, and the locking means of the fastening ring and the locking means of the closure cap being configured in such a way that they cannot be unlocked without sustaining damage, i.e. after being unlocked, they cannot be locked together again without sustaining damage.

The locking means can be formed by locking tabs and by locking recesses which enclose the latter with a form fit, the locking tabs being connected either to the fastening ring or to the closure cap, and the locking recesses being connected to the other part, i.e. the fastening ring or closure cap, such that the closure cap is locked together with the fastening ring and cannot be unlocked without sustaining damage.

The locking recesses can be undercut in the longitudinal direction. Moreover, the locking recesses can be undercut in the radial direction.

The fastening ring preferably comprises a proximal, annular portion, and a hollow cylindrical fastening wall which extends distally from the annular portion.

It may be expedient if the locking tabs are connected to an outer annular bead of the closure cap and, starting from the annular bead, they extend parallel to the longitudinal axis in the proximal direction and at a distance from an outer face of the closure cap, the locking recesses being open toward a distal front end face of the fastening wall.

In the fastening wall, locking recesses can be formed which enclose, with a form fit, locking tabs formed on an outer face of the closure cap. The fastening ring and the closure cap can comprise interacting thread elements which define a thread pitch.

Each locking tab expediently has a stop face which extends at an angle of inclination and which, when the closure cap is unscrewed from the fastening ring as guided by the thread elements, bears against a side face of the locking recess enclosing the respective locking tab, said angle of inclination being greater than the thread pitch, such that the locking tabs and/or the locking recesses are forcibly deformed during unscrewing.

The fastening ring can be placed and fixed on a distal tip of the syringe body through which the distal opening extends.

In order to receive a distal tip of the syringe body, the closure cap preferably has the shape of a hollow cylinder closed at one end.

In the closure cap, there is expediently a cylinder-shaped closure plug on which a central protruding portion is arranged for engaging in the distal opening of the syringe body. In a preferred embodiment of the invention, the closure cap has a central portion which is assigned to the distal opening of the syringe body and which is intended to engage in the distal opening.

The closure cap can have outer longitudinal ribs and be made from thermoplastic elastomers.

The fastening ring and the closure cap are expediently produced, in a two-component injection-molding operation, from different materials that do not integrally connect with one another.

The object is further achieved by a method for producing a syringe tip cap according to the invention, wherein the closure cap and the fastening ring are produced together, by means of a two-component injection-molding operation, in an interlocked manner in such a way that they cannot be unlocked without sustaining damage and, after being unlocked, cannot be locked together again without sustaining damage.

After production of the closure cap and of the fastening ring, a closure plug is preferably inserted into the closure cap.

In an advantageous embodiment, the syringe body is sealed off by the closure cap which, for this purpose, has a portion which is assigned to the distal opening of the syringe body and which is intended to engage in the distal opening. In this way, reliable sealing is guaranteed without the aforementioned closure plug. The closure cap is made from thermoplastic elastomers.

Other features which are considered as characteristic for the invention are set forth in the appended claims.

Although the invention is illustrated and described herein as embodied in a syringe tip cap and method for producing a syringe tip cap, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
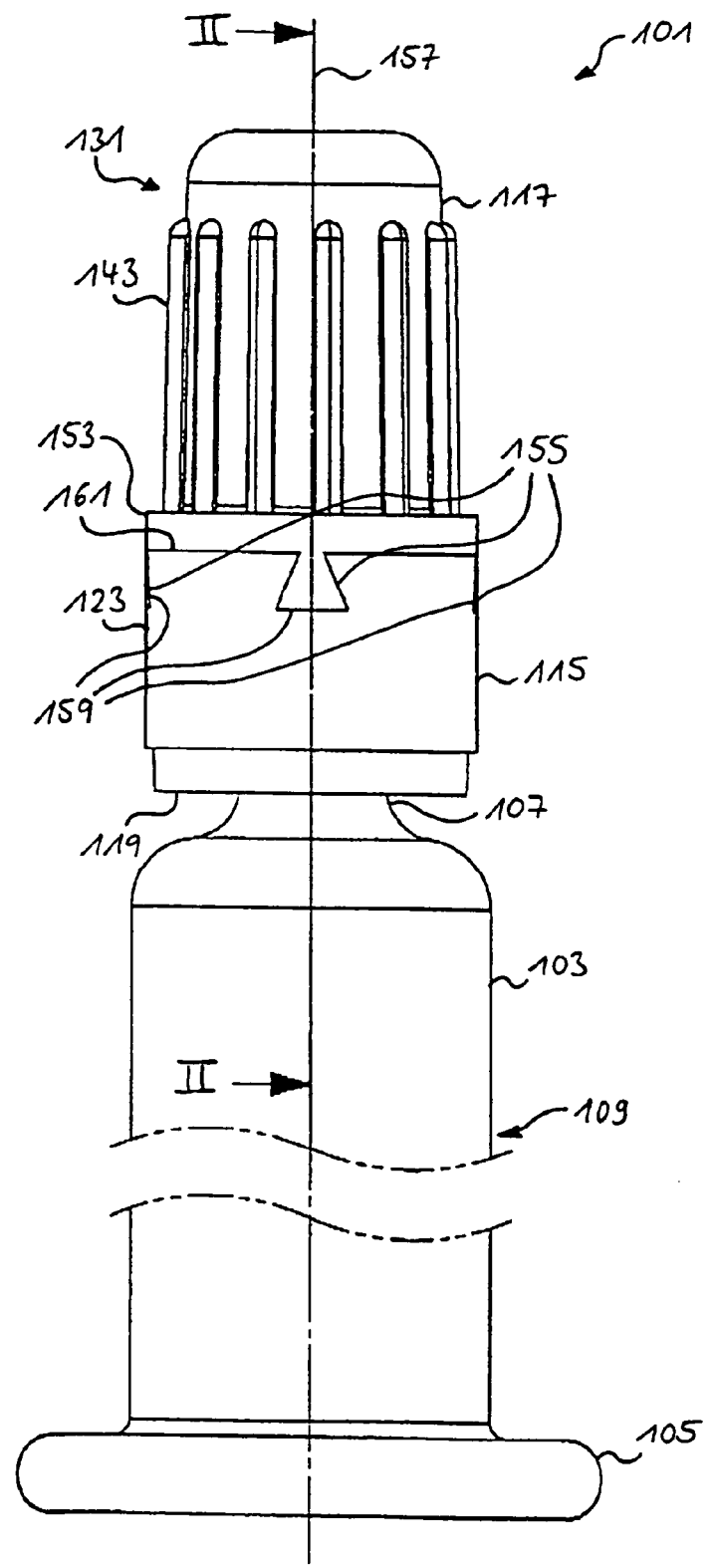
FIG. 1 shows a side view of a first embodiment of a syringe tip cap according to the invention, placed on a syringe body.
Figure 2:
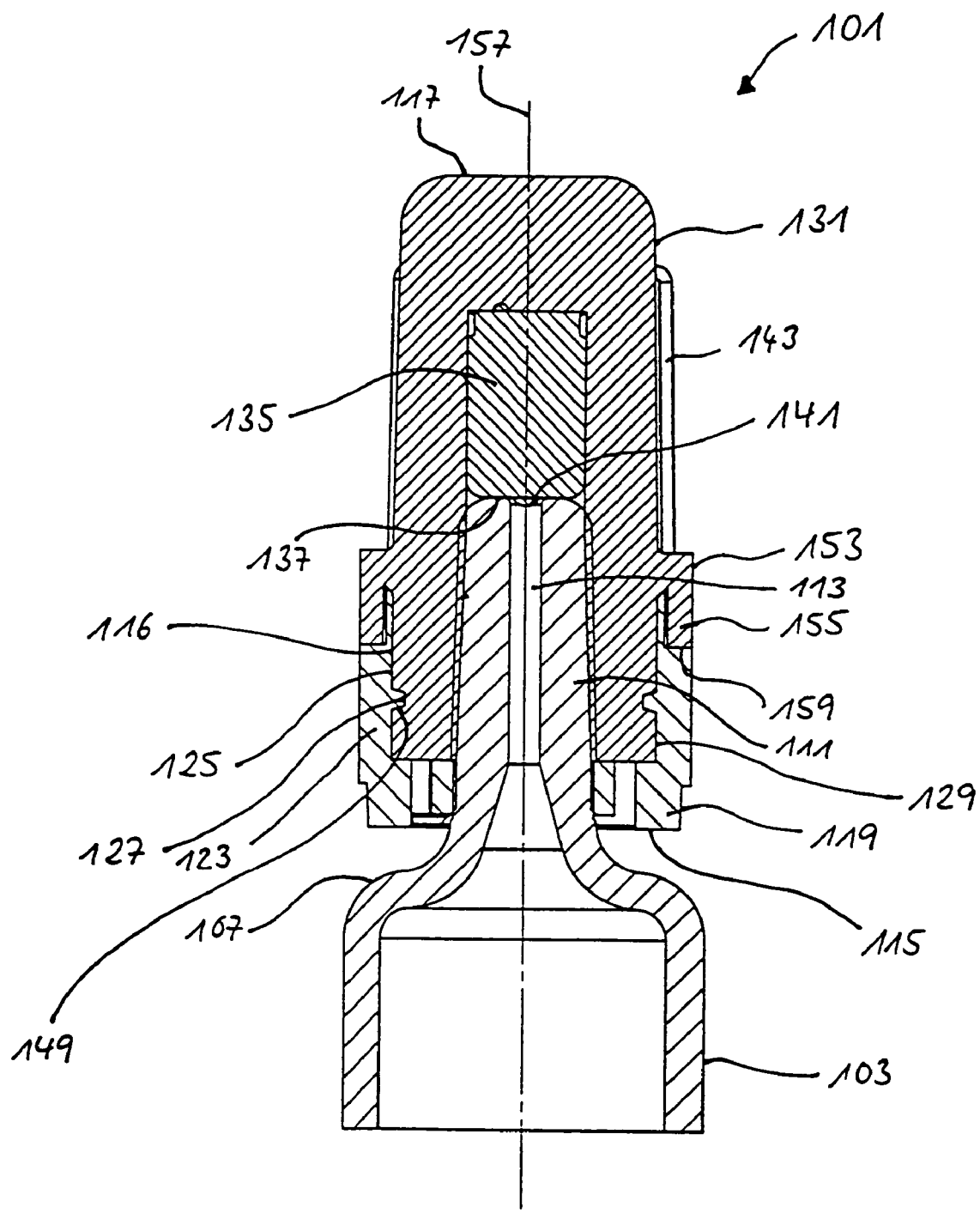
FIG. 2 shows a longitudinal section through the syringe tip cap from FIG. 1, along the line II-II in FIG. 1.

FIGS. 1 and 2 show, in a first embodiment of the invention, an inventive syringe tip cap 101 which is placed on a syringe barrel or syringe body 103. The syringe body 103 has a proximal end portion 105 and a distal end portion 107 which are connected by a hollow cylinder 109 which contains a syringe liquid (not shown). The distal end portion 107 is provided with a distal tip 111 wherein a distal opening 113 is formed.

The syringe tip cap 101 first comprises a fastening ring 115, customarily referred to as a luer lock ring or luer lock adapter, and a closure cap 117 which is connected to the fastening ring 115 in such a way that it cannot be released from the latter without being destroyed, as will be explained in detail below. The fastening ring 115 comprises a proximal, annular portion 119 which, when placed on the distal tip 111 of the syringe body 103, is held securely on the tip by frictional forces. For this purpose, an outer annular portion can have radially inwardly projecting contact portions which permit optimal fixing of the fastening ring on the tip. Moreover, the syringe body can have, in the area of the distal tip, an outer annular bead (not shown) which the fastening ring can engage around with a form fit, thus leading to further improved fixing. This is known per se, and so the securing of the fastening ring on the syringe body will not be described in detail here.

The annular portion 119 of the fastening ring 115 is adjoined distally by a hollow cylindrical fastening wall 123 whose inner face 125 has thread elements 127.

The closure cap 117 has the shape of a hollow cylinder closed at one end, and, in the assembled state, the distal tip 111 of the syringe body 103 is arranged inside the hollow cylinder. The closure cap 117 has a proximal portion 129 and a distal portion 131. A closure plug 135, which is let into the closure cap 117, has, at a proximal end face 137, a central protruding portion 141 which, when fitted, engages in the distal opening 113 of the distal tip 111 in order to reliably seal the syringe body 103. The closure plug can be formed in one piece with the closure cap.

As complements to the thread elements 127 of the fastening ring 115, the proximal portion 129 of the closure cap 117 has thread elements 149 for holding the closure cap 117 in the fastening ring 115. As an alternative to thread elements, the proximal portion 129 of the closure cap 117 can have outwardly protruding engagement portions which engage in thread elements of the fastening ring 115 in order to hold the closure cap 117 in the fastening ring 115, or, conversely, the fastening ring could have engagement portions which protrude inwardly from its fastening wall and interact with thread elements of the closure cap.

Formed on the outside of the distal portion 131 of the closure cap 117, there are longitudinal ribs 143 which improve handling when unscrewing the closure cap 117 from the fastening ring 115.

The closure cap 117 has a circumferential, flange-like annular bead 153 from which four locking tab 155 (alternatively, more or fewer locking tabs may also be provided) issue in the proximal direction parallel to a longitudinal axis 157 and at a radial distance from an outer face 116 of the closure cap 117. The locking tabs 155 are triangular in radial view (FIG. 1) and thus have a cross section increasing in size as the axial distance from the annular bead 153 increases, adjacent locking tabs 155 each being at an identical angle distance from one another.

In the fastening wall 123 of the fastening ring 115 there are locking recesses 159 which enclose the locking tabs 155 with a form fit (i.e., form lock, positive lock). The locking recesses are open toward a distal front end face 161, and the cross section of the locking recesses 159 increases in size as the axial distance from the end face 161 increases, i.e. the locking recesses are undercut in the longitudinal direction. By virtue of the described configuration, the locking tabs 155 are as it were interlocked with the locking recesses 159. The locking recesses 159 are additionally open toward the outer face of the fastening wall 123, such that the locking tabs 155 and in particular their connection to the annular bead 153 are visible to the user from the outside. Outer surfaces of the locking tabs 155 visible from the outside are also flush with the outer face of the fastening wall 123.

The above-described shape of the locking tabs 155 and locking recesses 159 has the effect that the closure cap 117 cannot be unscrewed from the fastening ring 115 without the locking tabs 155 and/or locking recesses 159 being damaged. Either the locking tabs 155 tear when being unscrewed from the closure cap 117, or the locking tabs 155 and/or the locking recesses 159 are irreversibly deformed when being unscrewed. Such damage shows the user that the syringe body 103 has already been opened once, and it makes any use of or tampering with the syringe content evident.

The closure cap 101 according to the invention cannot be produced by first producing the fastening ring 115 and the closure cap 117 separately from each other, for example in a known injection-molding operation, and then joining them together, because the locking tabs 115 cannot be engaged in the locking recesses 159 without sustaining damage. Therefore, the closure cap 117 and the fastening ring 115 are produced at the same time in a known two-component injection-molding operation to form the complete syringe tip cap 101. In doing this, materials for the closure cap 117 and the fastening ring 115 have to be used which do not join integrally to one another during the two-component injection-molding operation, so as to permit unscrewing of the closure cap 117 from the fastening ring 115 in later use. The closure cap 117 can therefore be made, for example, from a thermoplastic elastomer and the fastening ring 115 can be made from polycarbonate. After the fastening ring 115 and the closure cap 117, locked together in one another, have been produced simultaneously in a two-component injection-molding operation, the closure plug 135 is inserted into the closure cap 117.

To perform an injection procedure, the closure cap 117 is unscrewed from the fastening ring 115, and a needle, provided with a thread element, is screwed into the fastening ring 115 so that the syringe body 103 communicates with the needle via the distal opening 113. The liquid to be injected can then be injected using a syringe plunger.

Figure 3:
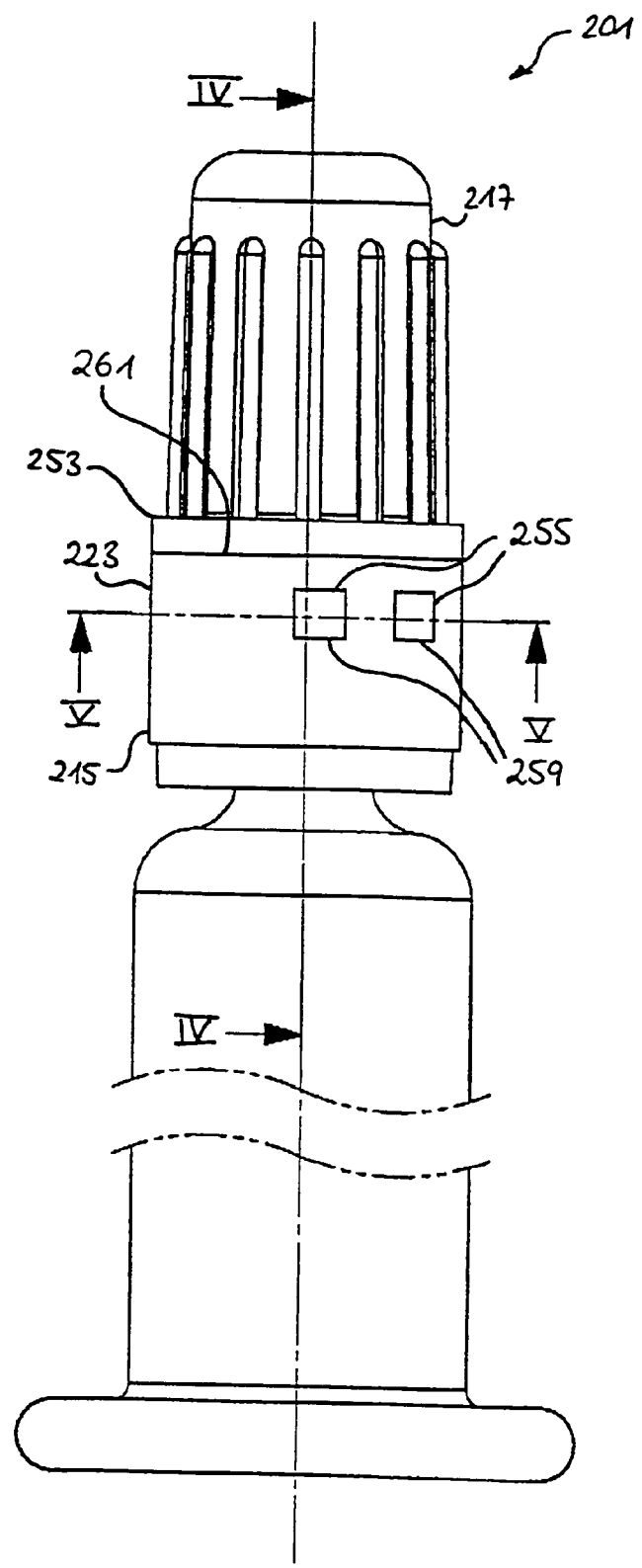
FIG. 3 shows a side view of a second embodiment of the syringe tip cap according to the invention, placed on a syringe body.
Figure 4:
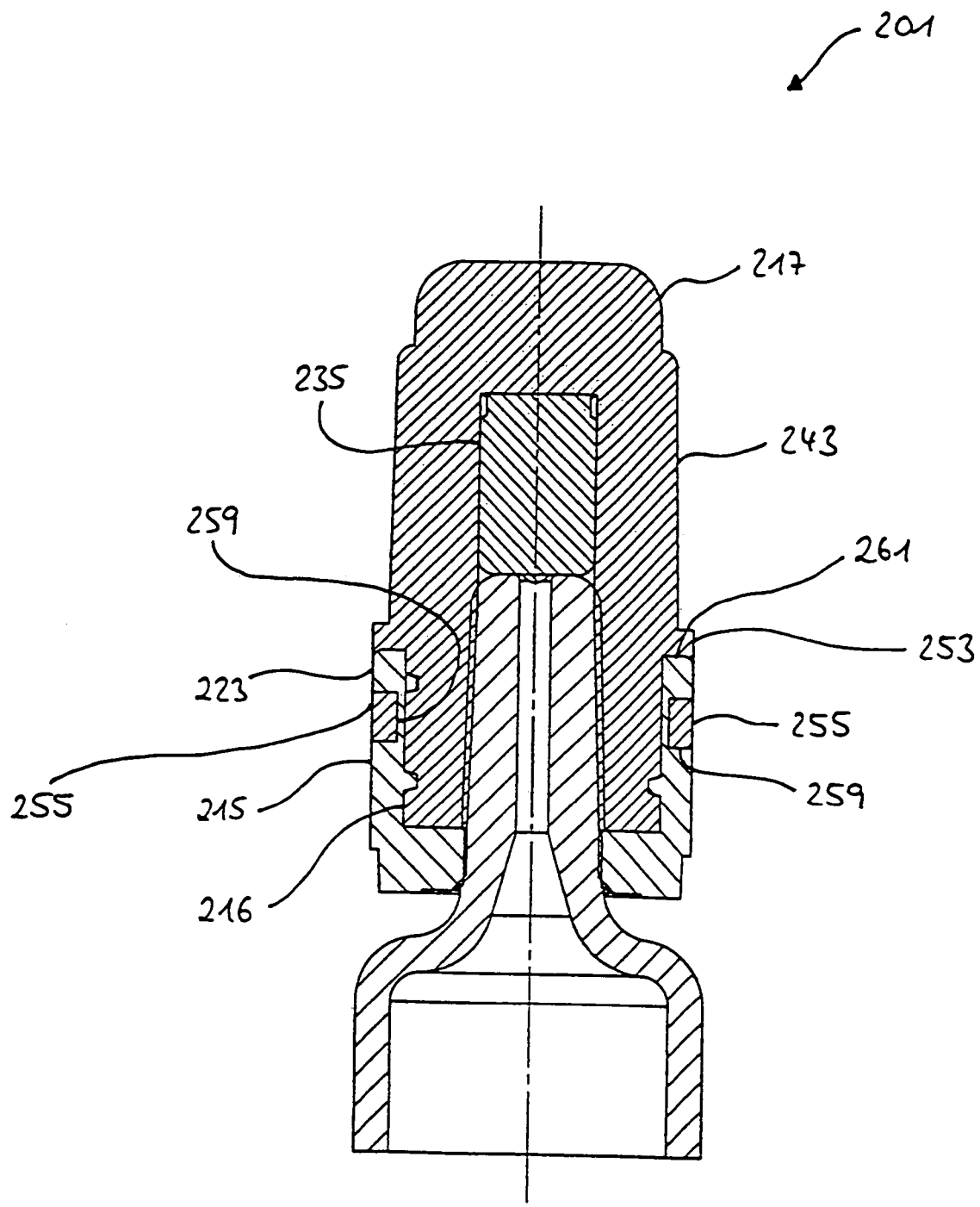
FIG. 4 shows a longitudinal section through the syringe tip cap from FIG. 3, along the line IV-IV in FIG. 3.
Figure 5:
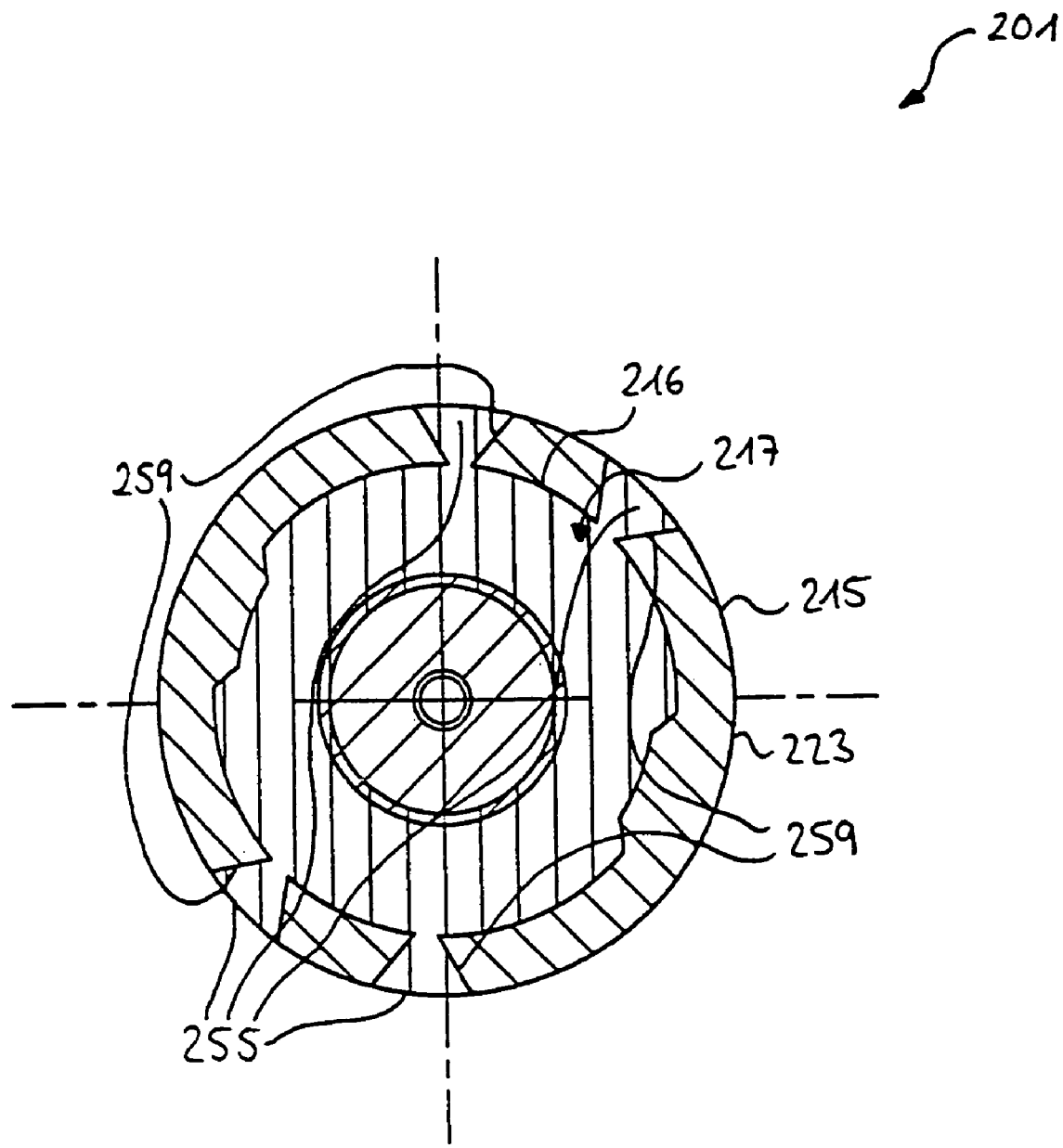
FIG. 5 shows a longitudinal section through the syringe tip cap from FIGS. 3 and 4, along the line V-V in FIG. 3.

FIGS. 3 to 5 show another embodiment of a syringe tip cap 201 with a fastening ring 215, a closure cap 217 and a closure plug 235. This syringe tip cap 201 differs from the syringe tip cap 101 shown in FIGS. 1 and 2 in that it has differently configured locking tabs 255 and differently configured locking recesses 259. The other features of the syringe tip cap 201 are substantially identical to the corresponding features of the syringe tip cap 101, so that in these respects reference is made to the above description.

The locking tabs 255 of the closure cap 217 are arranged in an area of the outer face 216 of the closure cap 217 completely enclosed by the fastening wall 223. Starting from the outer face 216 of the closure cap 217, they extend in a radial direction in respect of the hollow cylinder shape of the closure cap 217. It is additionally provided that a cross-sectional surface of the respective locking tab 255, oriented perpendicular to the radial direction, becomes larger the further it is from the outer face of the closure cap 217 (undercut in radial direction).

The locking tabs 255 are enclosed with a form fit by locking recesses 259 which are formed in the fastening wall 223 of the fastening ring 215. The cross-sectional surface of the locking recess 259 oriented perpendicular to the radial direction also becomes larger as the distance from the outer face of the closure cap 217 increases. The locking recesses 259 extend through the fastening wall 223 of the fastening ring 215 completely, so that the locking tabs 255 are visible from outside. The locking tabs 255 end flush with the outer face of the fastening wall 223.

The closure cap 217 has a circumferential annular bead 253 arranged between the thread elements 249 and the longitudinal ribs 243 of the closure cap 217. The annular bead 253 bears on a front end face 261 of the fastening wall 223.

Figure 6:
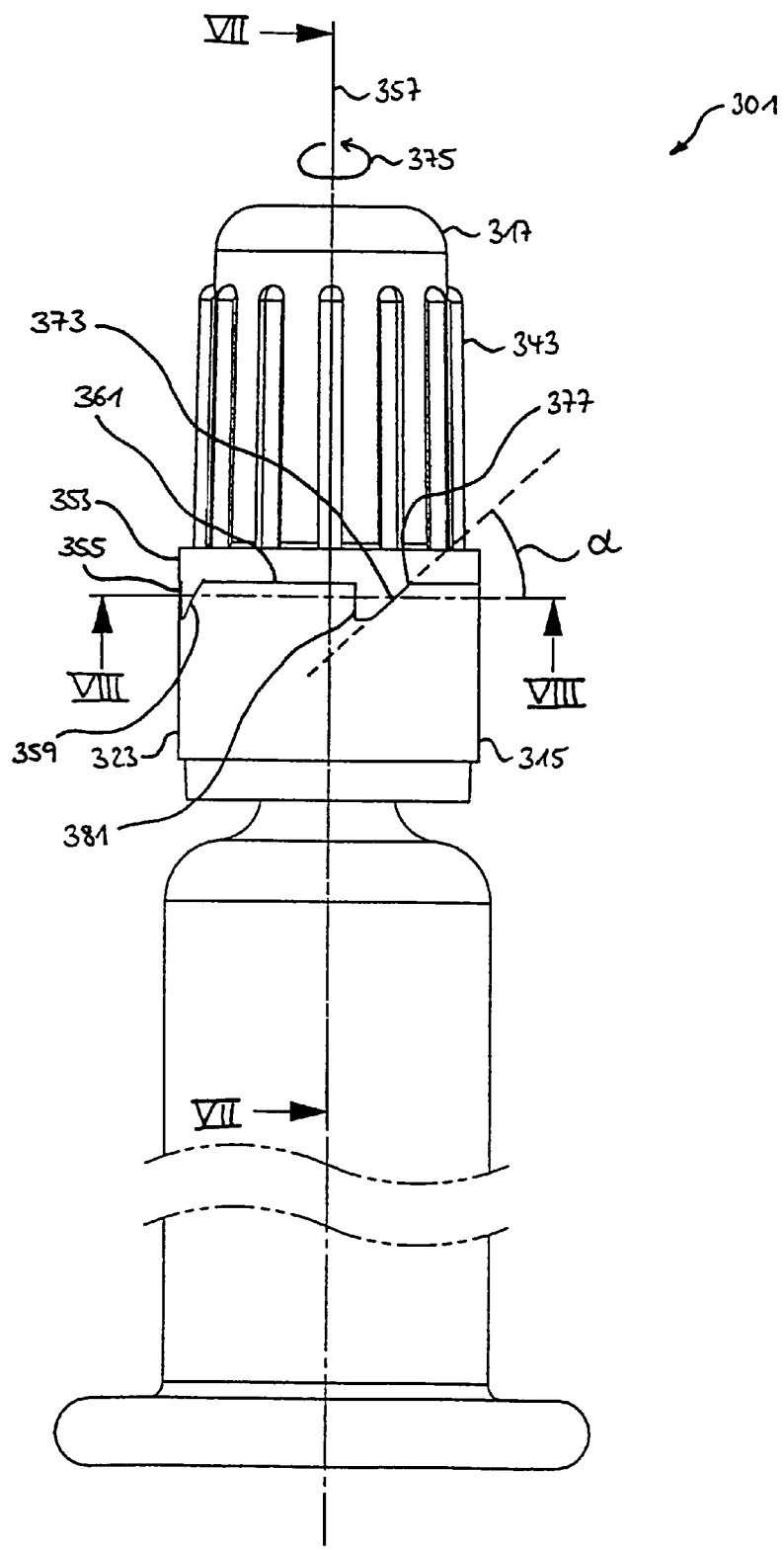
FIG. 6 shows a side view of a further embodiment of the syringe tip cap according to the invention, placed on a syringe body.
Figure 7:
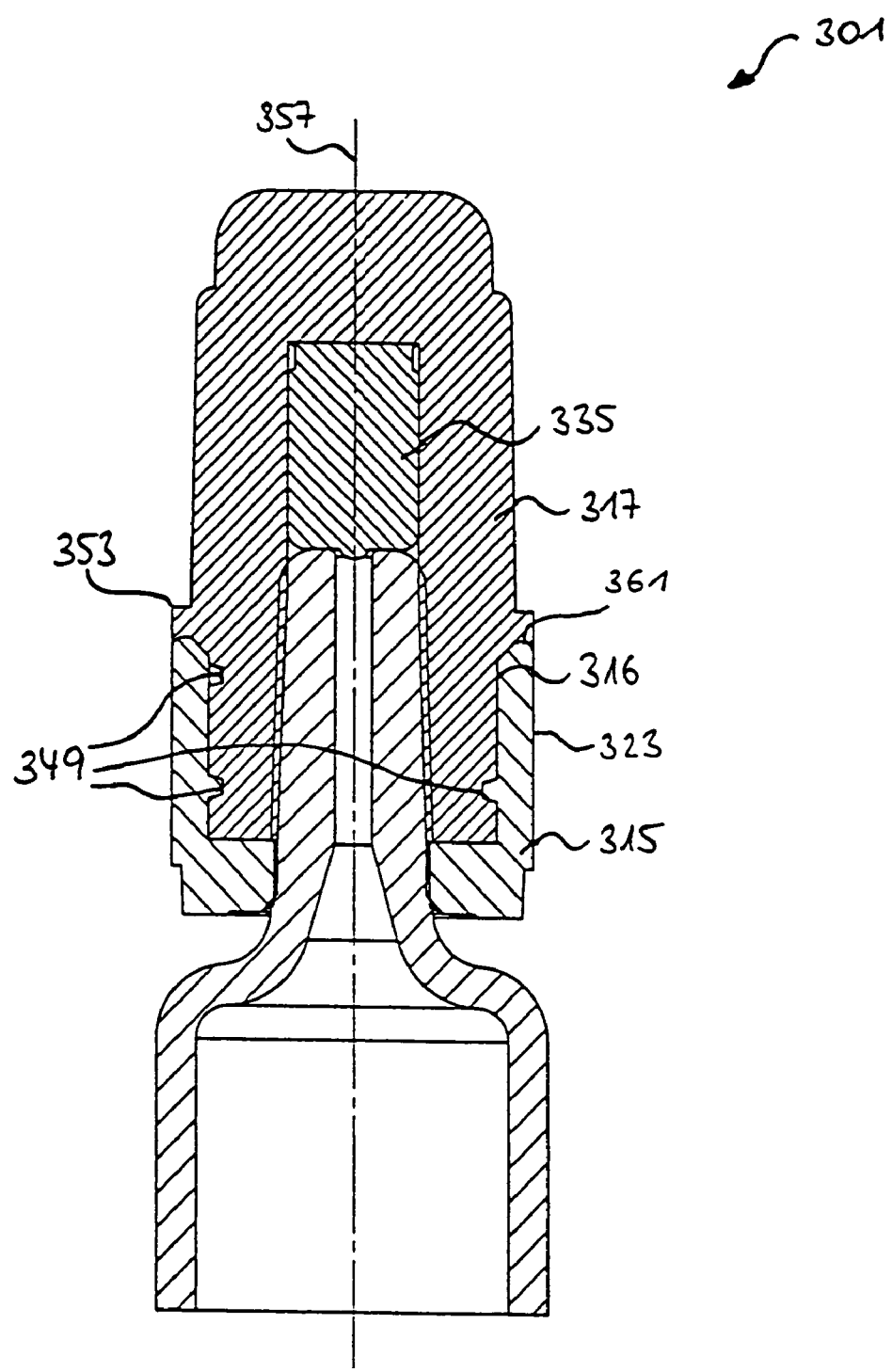
FIG. 7 shows a cross-sectional view of the syringe tip cap from FIG. 6, along the line VII-VII in FIG. 6.
Figure 8:
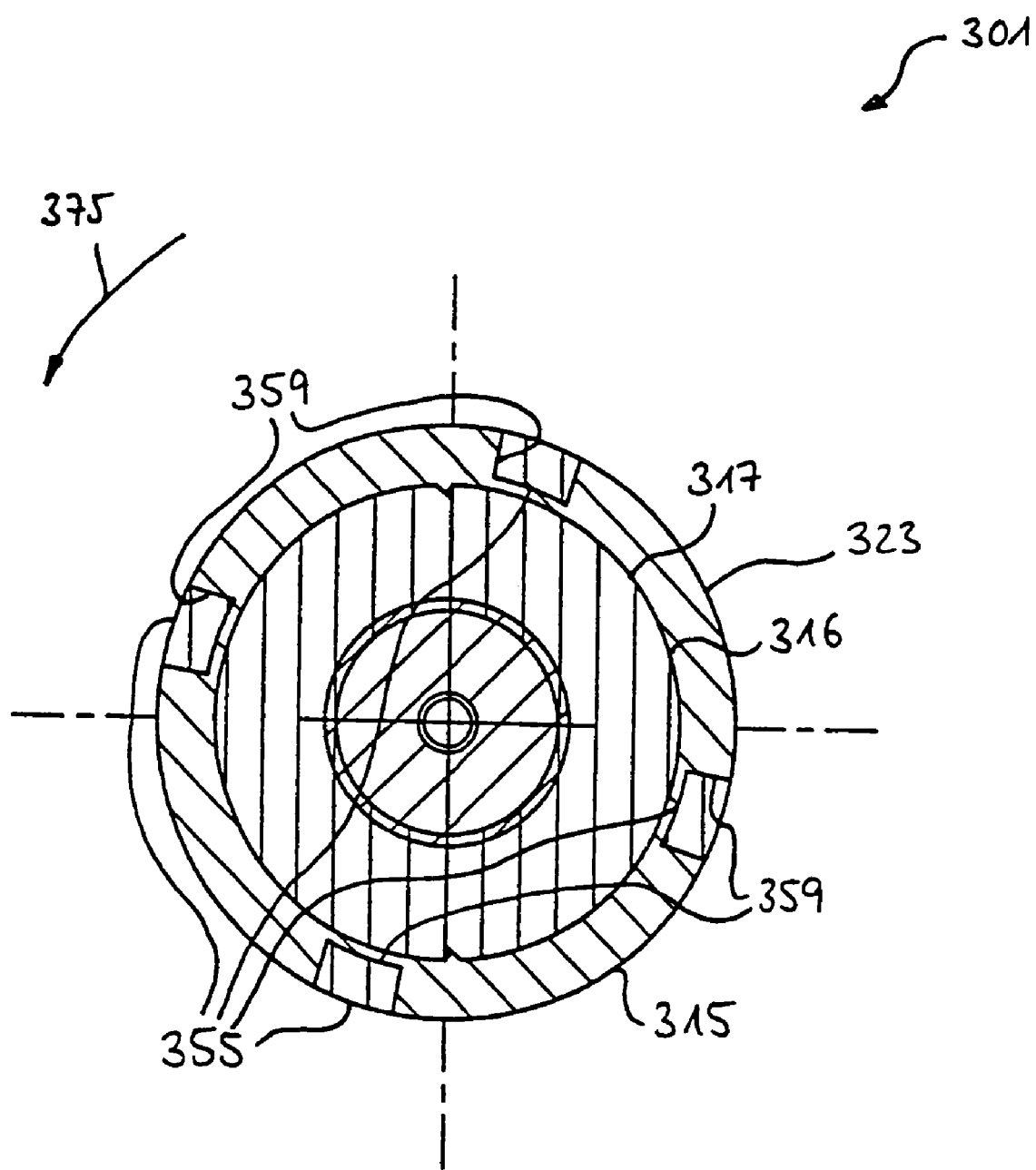
FIG. 8 shows a longitudinal section through the syringe tip cap from FIGS. 6 and 7, along the line VIII-VIII in FIG. 6.

FIGS. 6 to 8 show a further embodiment of a syringe tip cap 301 with a fastening ring 315, a closure cap 317 and a closure plug 335. This syringe tip cap 301 differs from the previously explained syringe tip caps 101 and 201 in that it has differently configured locking tabs 355 and differently configured locking recesses 359. The other features of the syringe tip cap 301 are substantially identical to the corresponding features of the syringe tip caps 101 and 201, so that in these respects reference is made to the above descriptions.

The closure cap 317 has a circumferential annular bead 353 arranged between the thread elements 349 and the longitudinal ribs 343 of the closure cap 317. Starting from this annular bead 353, four locking tabs 355 extend in the proximal direction, parallel to the longitudinal axis 357 and spaced apart from the outer face 316 of the closure cap 317, the locking tabs 355 having a decreasing cross section as the distance from the annular bead 353 increases, and adjacent locking tabs 155 each being at an identical angle spacing from one another. Alternatively, more or fewer than four locking tabs 355 could also be formed.

When being unscrewed in direction of rotation 375 (in the counterclockwise direction as seen from above in FIG. 6), a beveled stop face 373 of each locking tab 355 exerts a pressure against an opposite, correspondingly beveled side face 377 of a locking recess 359 of the fastening ring 315. The pressure face has an angle of inclination $\alpha$ which is greater than a thread pitch defined by the thread elements 349, such that the locking tabs 355 and/or the locking recesses 359 are forcibly deformed when the closure cap 317 is unscrewed from the fastening ring 315, and use of or tampering with the syringe content is made evident. These locking tabs 355 and locking recesses 359 also engage in one another, or are as it were interlocked, so that they can be produced only in a two-component injection-molding operation.

The locking recesses 359 are formed in the fastening wall 323 of the fastening ring 315 and enclose the locking tabs 355 with a form fit. The locking recesses 359 are open toward a front distal end face 361, and their cross section decreases as the distance from the end face 361 increases. The locking recesses 359 extend through the fastening wall 323 such that the locking tabs 355 are visible from the outside to a user. Outer surfaces of the locking tabs 355 visible from the outside are flush with the outer face of the fastening wall 323.

Figure 9:
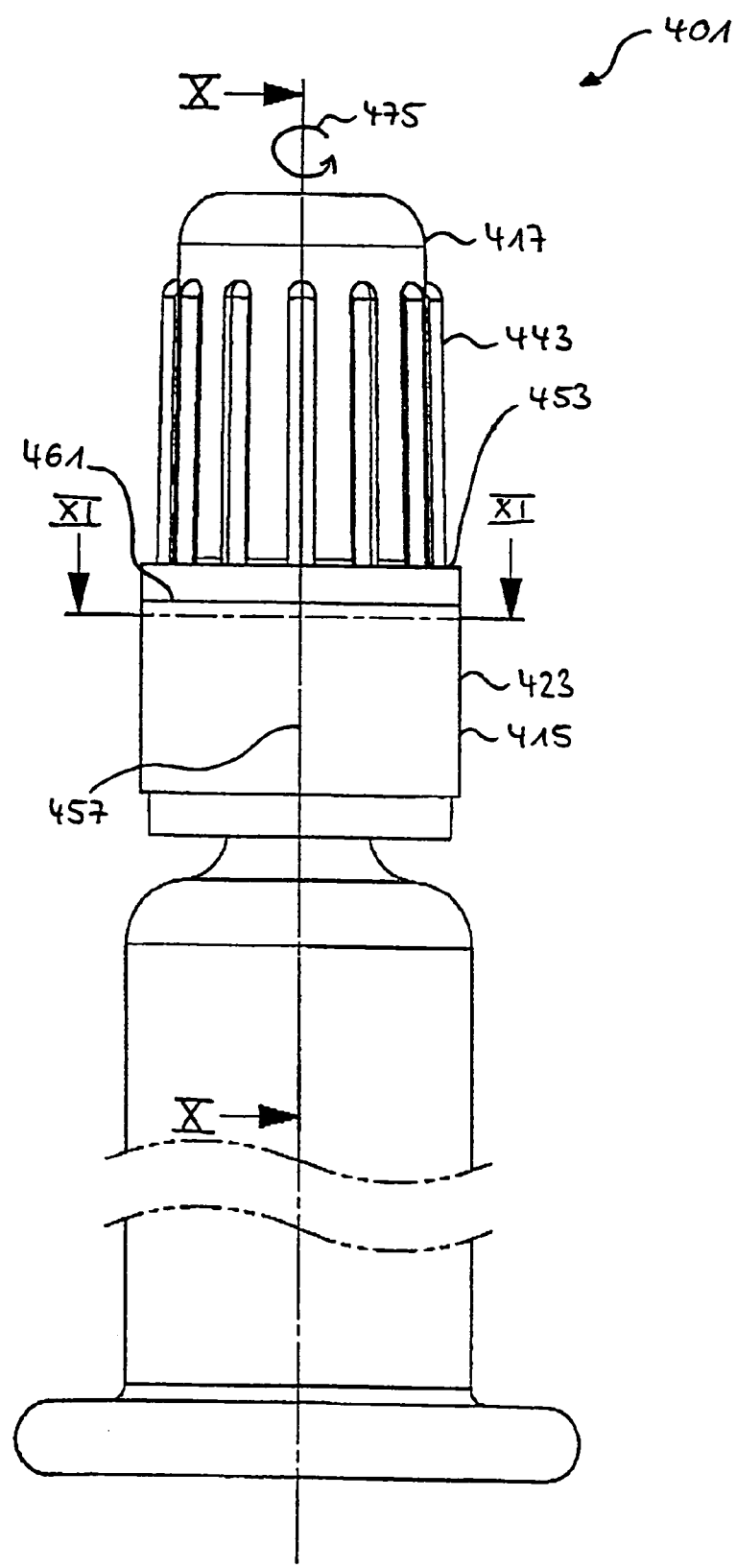
FIG. 9 shows a side view of a further embodiment of the syringe tip cap according to the invention, placed on a syringe body.
Figure 10:
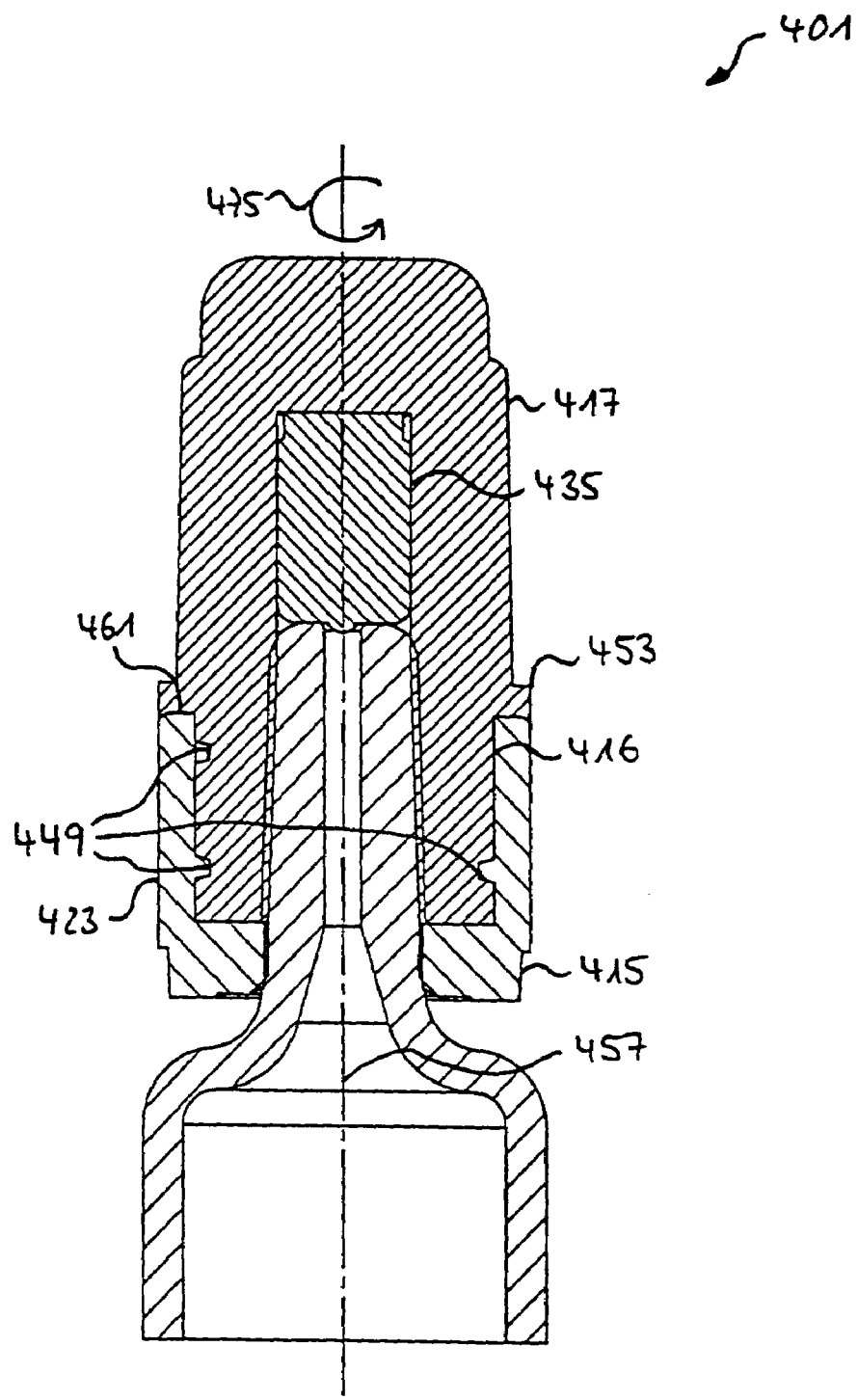
FIG. 10 shows a longitudinal section through the syringe tip cap from FIG. 9, along the line X-X in FIG. 9.
Figure 11:
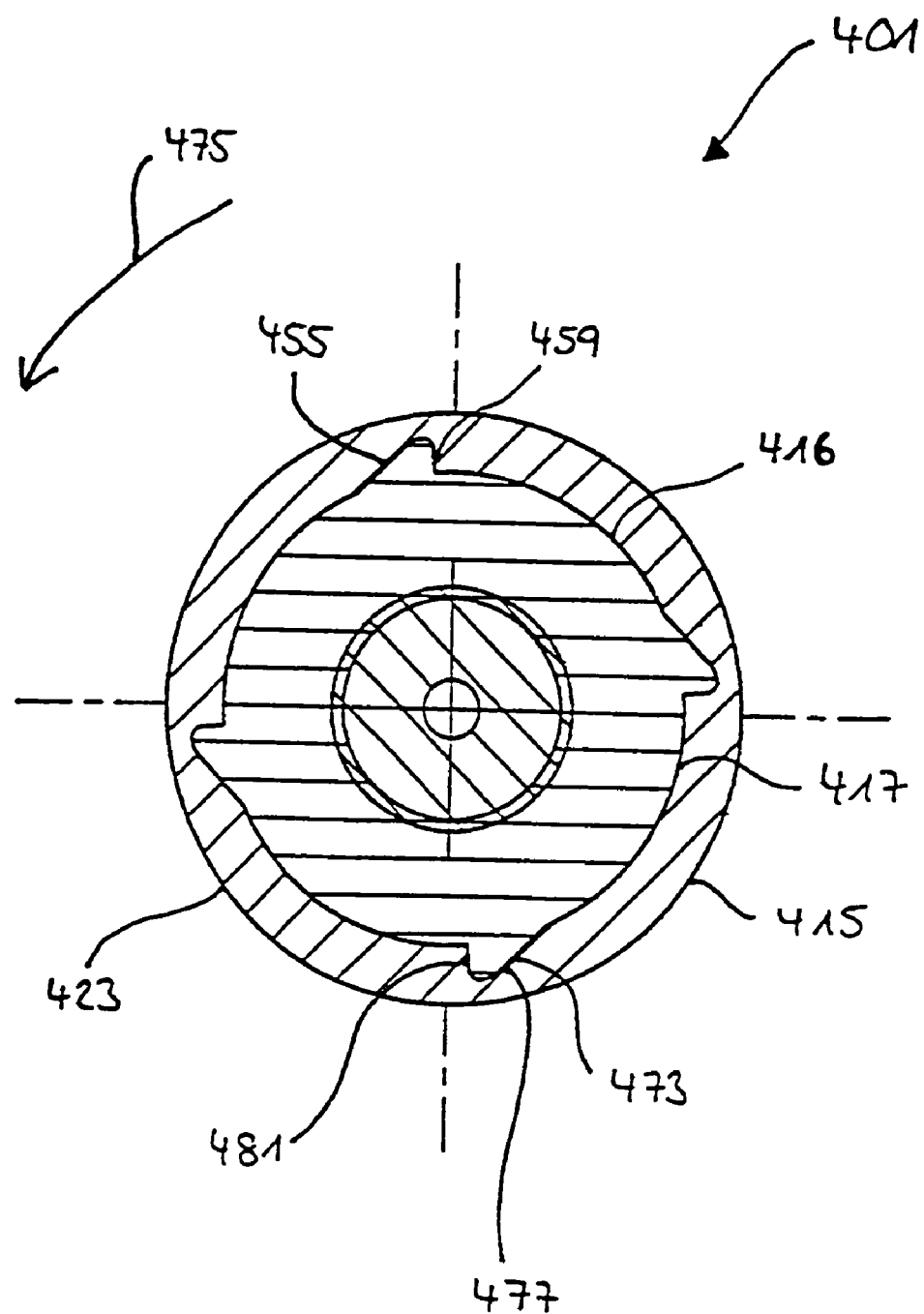
FIG. 11 shows a cross-sectional view of the syringe tip cap from FIGS. 9 and 10, along the line XI-XI in FIG. 9.

FIGS. 9 to 11 show a further embodiment of a syringe tip cap 401 with a fastening ring 415, a closure cap 417 and a closure plug 435. This syringe tip cap 401 differs from the syringe tip caps 101, 201 and 301 shown in FIGS. 1 to 8 in that it again has differently configured locking tabs 455 and locking recesses 459. The other features of the syringe tip cap 401 correspond substantially to those of the syringe tip caps 101, 201 and 301, so that in these respects reference is made to the above descriptions.

The locking tabs 455 of the closure cap 417, which have a wedge-shaped cross section or a rounded triangular cross section (FIG. 11), are arranged protruding radially from the outer face 416 of the closure cap 417 and are completely enclosed by the fastening wall 423 of the fastening ring 415.

A pressure face 473 of each locking tab 455 extends in a radial tangential ascent, and a side face 481 of each locking tab 455, lying opposite the pressure face 473, runs in a plane parallel to or containing the longitudinal axis 157. When the closure cap 417 is unscrewed from the fastening ring 415 in direction of rotation 475 (counterclockwise as seen from above in FIG. 9), the locking tabs 455 are pressed against corresponding side faces 477 of the locking recesses 459 of the fastening ring 415 and, if appropriate, are deformed or destroyed together with the locking recesses 459.

The locking recesses 459 enclose the locking tabs 455 with a form fit and are arranged, with a complementary configuration to these, in the fastening wall 423 of the fastening ring 415. The locking recesses 459 are only depressions in the inner face of the fastening wall 423 and do not pass completely through the latter.

The closure cap 417 comprises a circumferential annular bead 453 which is arranged between the thread elements 449 and the longitudinal ribs 443 of the closure cap 417. The annular bead 453 bears on a front end face 461 of the fastening wall 423.

The term "interlocked" and similar expressions relate, in the context of the invention, to formations (locking means) which engage spatially in one another and behind one another and are undercut in the longitudinal direction, in particular locking tabs and locking recesses which engage in one another, in such a way that the locking means cannot be released from one another without sustaining damage. Conversely, the syringe tip cap according to the invention cannot be produced by separately producing the fastening ring and closure cap and then joining and locking them together, since the locking means would also be identifiably damaged or destroyed here. As has already been mentioned, production is feasible only in a two-component injection-molding operation.

Figure 12:
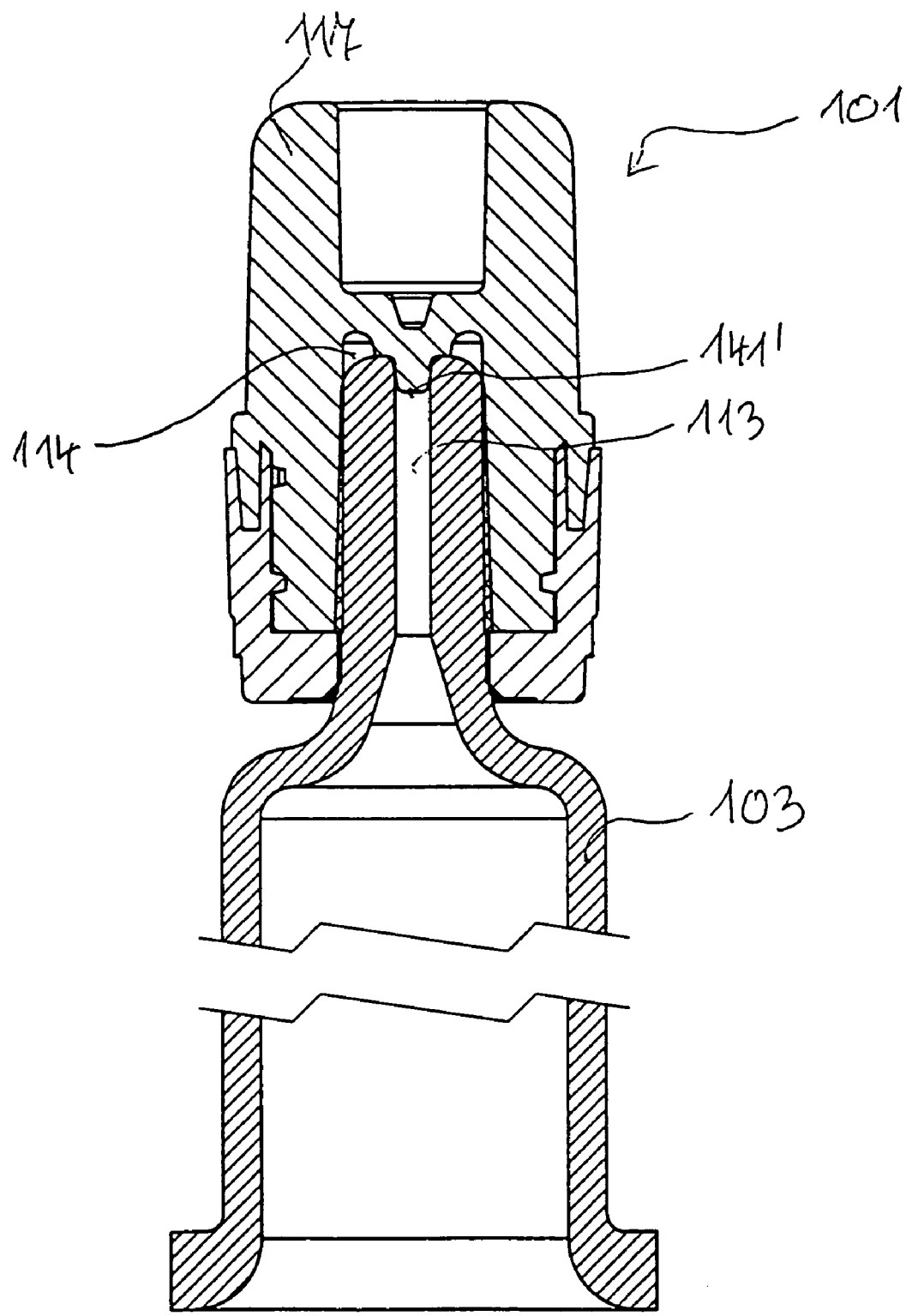
FIG. 12 shows a longitudinal section through a variant embodiment of the means of sealing the syringe body.

FIG. 12 shows a variant of the means of sealing the syringe body 103. The sealing is effected by the closure cap 117 which, for this purpose, has a portion 141' which is assigned to the distal opening 113 of the syringe body 103 and is intended to engage in the distal opening 113. Even without the closure plug 135, a reliable seal is ensured. The clearance 114 can be configured as an annular groove or also as a plurality of individual grooves to increase the elasticity.

This application claims the priority, under 35 U.S.C. §119, of European patent application No. 04 012 833.2, filed May 29, 2004, and European patent application No. 05 010 397.7, filed May 12, 2005; the disclosures of the prior applications are herewith incorporated by reference in their entirety.

We claim:

1. A syringe tip cap for sealingly closing a distal opening of a syringe body, the syringe tip cap comprising:
 a fastening ring to be arranged and fastened on the syringe body about the distal opening; and
 a closure cap releasably connected to said fastening ring and sealingly closing the distal opening;
 said fastening ring having a first locking device interlocked with a second locking device of said closure cap, and wherein said first locking device and said second locking device are configured not to be unlocked without sustaining damage and, after unlocking, cannot be returned to an initial locked state;
 wherein said first locking device includes locking recesses formed in a distal end face of said fastening ring and said second locking device includes locking tabs engaged within said locking recesses with a form fit; and
 wherein said locking tabs project from said closure cap parallel to the longitudinal axis in the proximal direction, said locking recesses are open at the distal front end face of said fastening ring, and said locking tabs project across the distal front end face of said fastening ring and into said locking recesses.

2. The syringe tip cap according to claim 1, wherein said locking tabs are undercut in a longitudinal direction of the syringe.

3. The syringe tip cap according to claim 1, wherein said locking tabs are undercut in a radial direction of the syringe.

4. The syringe tip cap according to claim 1, wherein said fastening ring includes a proximal, annular portion, and a hollow cylindrical fastening wall extending distally from said annular portion.

5. The syringe tip cap according to claim 1, wherein said fastening ring includes a proximal, annular portion, and a hollow cylindrical fastening wall extending distally from said annular portion, said locking tabs are connected to an outer annular bead of said closure cap and, starting from the annular bead a distance from an outer face of said closure cap.

6. The syringe tip cap according to claim 4, wherein a fastening wall is formed with locking recesses and said locking recesses enclose, with a form fit, locking tabs formed on an outer face of said closure cap.

7. The syringe tip cap according to claim 1, wherein said fastening ring and said closure cap comprise interacting thread elements defining a thread pitch.

8. The syringe tip cap according to claim 1, wherein said fastening ring and said closure cap comprise mutually meshing thread elements defining a thread pitch, each locking tab has a stop face extending at an angle of inclination and which, when said closure cap is unscrewed from said fastening ring as guided by the thread elements, bears against a side face of said locking recess enclosing the respective said locking tab, and wherein said angle of inclination is greater than the thread pitch so as to forcibly deform said locking tabs and/or said locking recesses during unscrewing.

9. The syringe tip cap according to claim 1, wherein said fastening ring is configured to be placed and fixed on a distal tip of said syringe body through which said distal opening extends.

10. The syringe tip cap according to claim 1, wherein said closure cap, in order to receive a distal tip of said syringe body, has a shape of a hollow cylinder closed at one end.

11. The syringe tip cap according to claim 10, which comprises a cylinder-shaped closure plug in said closure cap, and a central protruding portion arranged on said cylinder-shaped closure plug for engaging in said distal opening of said syringe body.

12. The syringe tip cap according to claim 10, wherein said closure cap has a central portion assigned to said distal opening of said syringe body and configured for engagement in said distal opening.

13. The syringe tip cap according to claim 1, which comprises outer longitudinal ribs formed on said closure cap.

14. The syringe tip cap according to claim 1, wherein said closure cap is made from a thermoplastic elastomer.

15. The syringe tip cap according to claim 1, wherein said fastening ring and said closure cap are produced, in a two-component injection-molding operation, from mutually different materials that do not integrally connect with one another.

16. A method of producing a syringe tip cap for a syringe body with a distal opening, the method which comprises:
 injection molding, in a two-component injection-molding operation:
 a fastening ring to be fastened on the syringe body about the distal opening; and a closure cap releasably connected to the fastening ring and sealingly closing the distal opening;

thereby forming the fastening ring with fastening recesses open at a distal end surface of the fastening ring, and forming the closure cap with locking tabs projecting from the closure can, parallel to a longitudinal direction and into the fastening recesses;

wherein the closure cap and the fastening ring are produced together and the locking tabs and the fastening recesses are interlocked in one another so that the fastening ring and the closure cap cannot be unlocked without sustaining damage and, after being unlocked, cannot be joined without sustaining damage.

17. The method according to claim 16, which comprises, after producing the closure cap and the fastening ring, inserting a closure plug into the closure cap.

* * * * *